(12) United States Patent
Burke et al.

(10) Patent No.: US 8,673,014 B2
(45) Date of Patent: Mar. 18, 2014

(54) METHOD OF CRANIAL REPAIR AND CRANIAL REPAIR IMPLANT MOLDING DEVICE

(75) Inventors: Shawn Burke, Jacksonville, FL (US); Michael Teague, Jacksonville, FL (US); Pat Lemoyne, Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 124 days.

(21) Appl. No.: 13/437,098

(22) Filed: Apr. 2, 2012

(65) Prior Publication Data

US 2012/0265313 A1   Oct. 18, 2012

Related U.S. Application Data

(60) Provisional application No. 61/516,295, filed on Apr. 1, 2011.

(51) Int. Cl.
*A61F 2/02* (2006.01)

(52) U.S. Cl.
USPC ............ 623/17.19; 623/17.16; 623/17.18; 623/23.51; 623/23.58; 623/23.61; 623/23.62; 623/279; 623/285; 623/903

(58) Field of Classification Search
CPC ........................ A61F 2/2875; A61F 2/2803
USPC ......... 623/17.16, 17.19, 23.51, 23.58, 23.61, 623/23.62; 606/279, 285, 903
See application file for complete search history.

(56) References Cited

U.S. PATENT DOCUMENTS

| | | | |
|---|---|---|---|
| 4,900,499 A | 2/1990 | Mills | |
| 5,503,164 A * | 4/1996 | Friedman | 128/898 |
| 5,895,387 A * | 4/1999 | Guerrero et al. | 606/71 |
| 6,350,284 B1 * | 2/2002 | Tormala et al. | 623/17.19 |
| 6,645,250 B2 * | 11/2003 | Schulter | 623/17.17 |
| 7,050,877 B2 * | 5/2006 | Iseki et al. | 700/118 |
| 7,097,792 B2 * | 8/2006 | Lin et al. | 264/42 |
| 7,122,139 B2 * | 10/2006 | Lin et al. | 264/42 |
| 7,346,391 B1 * | 3/2008 | Osorio et al. | 607/2 |
| 8,343,225 B2 * | 1/2013 | Linares | 623/17.19 |
| 8,398,720 B2 * | 3/2013 | Swords | 623/23.55 |
| 8,546,456 B2 * | 10/2013 | Rose et al. | 521/88 |
| 2001/0043940 A1 | 11/2001 | Boyce et al. | |
| 2002/0123750 A1 * | 9/2002 | Eisermann et al. | 606/69 |
| 2003/0208205 A1 * | 11/2003 | Gambale | 606/70 |
| 2005/0251266 A1 * | 11/2005 | Maspero et al. | 623/23.51 |
| 2006/0116682 A1 * | 6/2006 | Longo | 606/69 |
| 2006/0224242 A1 * | 10/2006 | Swords et al. | 623/17.19 |

(Continued)

FOREIGN PATENT DOCUMENTS

DE        2501291 A1    7/1976

*Primary Examiner* — Thomas J Sweet
*Assistant Examiner* — Seema Mathew
(74) *Attorney, Agent, or Firm* — Thomas C. Saitta

(57) ABSTRACT

A method of cranial repair and the cranial implant molding device used therein, the device having a frame or base that receives a bottom or convex molding plate and a top or concave molding plate in a manner whereby the two plates are separated a distance to receive a settable or curable implant forming material therebetween. The plates are separated by a compressible member such that by the use of threaded mechanical fasteners or similar members the distance between the two plates can be adjusted by tightening or loosening the mechanical members. The thickness of the implant is varied by varying the separation distance on different sides of the frame.

6 Claims, 1 Drawing Sheet

(56) References Cited

U.S. PATENT DOCUMENTS

| | | |
|---|---|---|
| 2007/0114685 A1 | 5/2007 | Wardrop et al. |
| 2007/0179621 A1 | 8/2007 | McClellan, III et al. |
| 2008/0262319 A1* | 10/2008 | Reichenberger et al. ..... 600/300 |
| 2009/0259263 A1* | 10/2009 | Steger et al. ................ 606/86 R |
| 2009/0299380 A1* | 12/2009 | Singhal et al. ................ 606/129 |
| 2010/0145162 A1* | 6/2010 | Devauchelle et al. ........ 600/300 |
| 2010/0266660 A1* | 10/2010 | McKay et al. ................ 424/426 |
| 2011/0028972 A1* | 2/2011 | Khanna .......................... 606/57 |
| 2011/0166669 A1* | 7/2011 | Truncale et al. ........... 623/23.51 |
| 2012/0184999 A1* | 7/2012 | Khanna ........................ 606/281 |
| 2012/0271418 A1* | 10/2012 | Hollister et al. ........... 623/17.11 |

* cited by examiner

METHOD OF CRANIAL REPAIR AND CRANIAL REPAIR IMPLANT MOLDING DEVICE

This application claims the benefit of U.S. Provisional Patent Application Ser. No. 61/516,295, filed on Apr. 1, 2011, the disclosure of which is incorporated herein by reference.

BACKGROUND OF THE INVENTION

This invention relates generally to the field of artificial implants for bone repair, and more particularly relates to implants that replace damaged or missing portions of bones, and even more particularly relates to implants for use in repairing the cranium. The invention relates generally to the field of molding devices for the manufacture of cranial implants as utilized in cranial repair methodologies.

In many situations it is medically necessary to replace a relatively large portion of the cranium that has either been removed by a surgeon for access to the brain or to address damaged due to disease, accident or physical attack. Typically a surgeon will be able to remove a portion of the skull in a controlled shape or configuration, such as for example a circle, triangle or the like. The surgeon then has the option of replacing the removed bone material with a pre-formed replacement implant that approximates the needed the shape.

A problem sometimes arises whereby the assortment of pre-formed implants does not properly accommodate the variations in thickness of the cranial bone. The pre-manufactured cranial implant may be too thick or too thin overall. The cranial bone may also vary in thickness, such that for example one side of the removed bone may be thicker than the other side.

It is an object of this invention to provide a cranial implant molding device that is adjustable such that cranial implants of different overall thicknesses can be produced. It is a further object to provide a cranial implant molding device that is adjustable such that opposing sides of a single implant may be produced having differing thicknesses.

SUMMARY OF THE INVENTION

A method of cranial repair and the device used in the method, the cranial implant molding device comprising a frame or base having a bottom or convex mold plate and a top or concave mold plate disposed in a manner whereby the two plates are separated a short distance to create a mold cavity to receive a settable or curable implant forming material. The top mold plate comprises a mold cavity top wall located between a pair of lateral top plate flanges and the bottom mold plate comprises a mold cavity bottom wall located between a pair of lateral bottom plate flanges. By the use of threaded mechanical fasteners or similar means the distance between the two mold plates can be adjusted by tightening or loosening the mechanical members. Preferably, at least one compressible member is disposed between each top plate flange and bottom plate flange. The thickness of the implant is varied by adjusting the separation distance of the flanges to be equal on both sides of the mold cavity to produce an implant with each side being of the same thickness. An implant varying in thickness from one side to the other is produced by setting the separation distance of the flanges on one side of the mold cavity different from the separation distance on the other side of the mold cavity. The molding device may comprise a plurality of mold plate sets, the sets varying in the amount of curvature, size, shape, etc.

When a surgeon removes a cranial bone portion the thickness and configuration of the removed bone portion is measured and the proper combination of top and bottom mold plates are chosen to best match the configuration. The separation distance between the mold plates is then adjusted to best match the thickness of the opposing edges of the removed bone portion, such that the resulting cranial implant so produced will require minimal post-curing shaping prior to implantation.

DETAILED DESCRIPTION OF THE INVENTION

Figure 1:
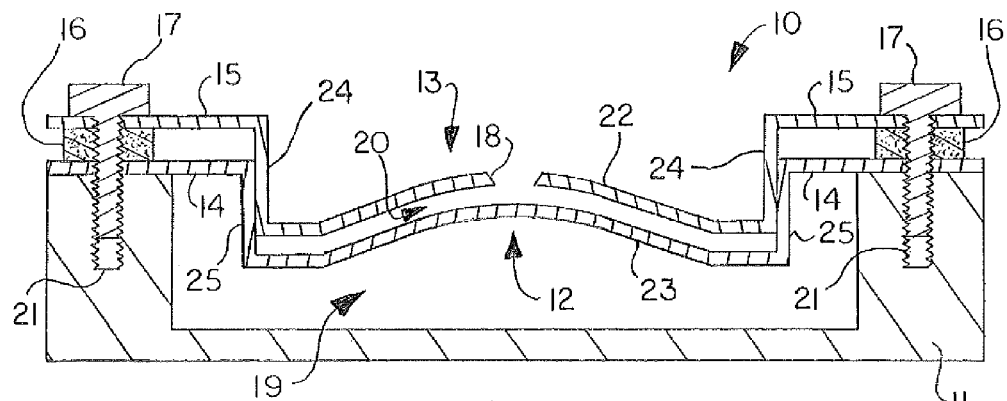
FIG. 1 is a cross-sectional view of an embodiment of the device.
Figure 2:
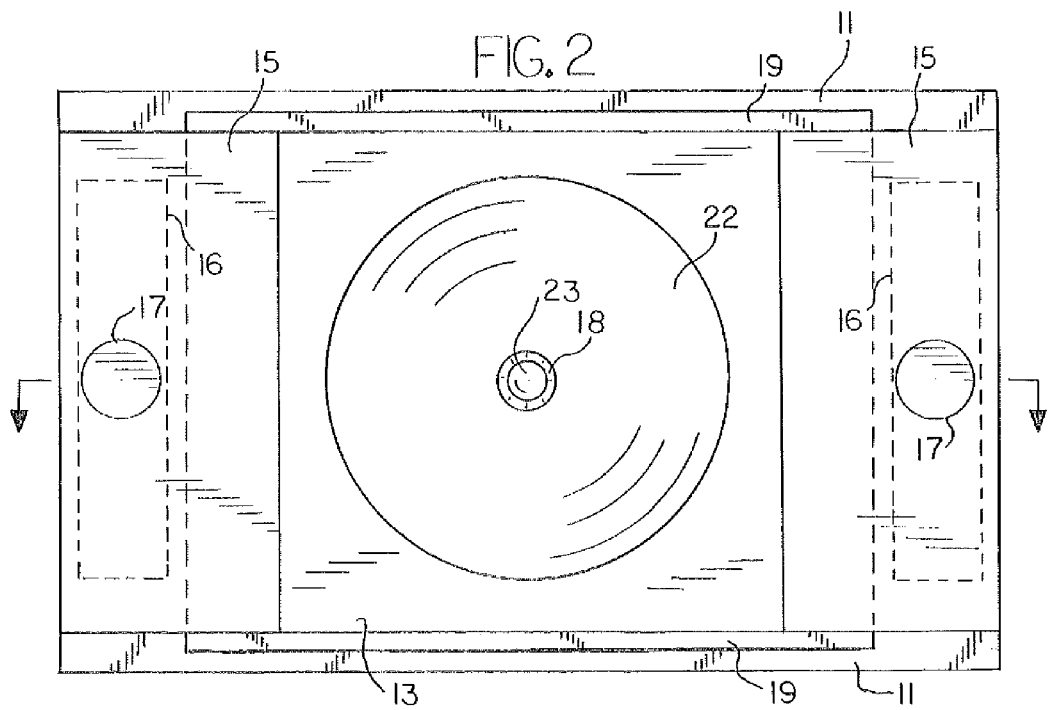
FIG. 2 is a top view of the embodiment of FIG. 1.

With reference to the drawings, the embodiments for the invention will now be described in detail. In a general sense, the invention is a method of cranial repair and the cranial implant molding device used therein comprising a frame or base that receives a bottom or convex mold plate and a top or concave mold plate in a manner whereby the two plates are separated a short distance to create a mold cavity to receive a settable or curable implant forming material. The top mold plate comprises a mold cavity top wall located between a pair of top plate flanges and the bottom mold plate comprises a mold cavity bottom wall located between a pair of bottom plate flanges. By the use of threaded mechanical fasteners or similar means the distance between the two mold plates can be adjusted by tightening or loosening the mechanical members. Preferably, at least one compressible member is disposed between each top plate flange and bottom plate flange. The thickness of the implant is varied by adjusting the separation distance of the flanges to be equal on both sides of the mold cavity to produce an implant with each side being of the same thickness. An implant varying in thickness from one side to the other is produced by setting the separation distance of the flanges on one side of the mold cavity different from the separation distance on the other side of the mold cavity. The molding device may comprise a plurality of mold plate sets, the sets varying in the amount of curvature, size, shape, etc.

The invention may be broadly defined as a cranial implant molding device, and its method of use in cranial repair surgery, comprising a bottom plate comprising a mold cavity bottom wall, a first and a second bottom plate flange positioned to either side of said mold cavity bottom wall, and a depending wall connecting each of said bottom plate flanges to said mold cavity bottom wall; a top plate comprising a mold cavity top wall, a first and a second top plate flange positioned to either side of said mold cavity top wall, a depending wall connecting each of said top plate flanges to said mold cavity top wall, and a vent port disposed in said mold cavity top wall; a base comprising a recess, said bottom plate and said top plate being positioned on said base such that said mold cavity bottom wall and said mold cavity top wall are disposed within said recess and such that said mold cavity bottom wall is separated from said mold cavity top wall to form a mold cavity adapted to receive implant forming material; at least one mechanical adjustment member extending through said first top plate flange and said first bottom plate flange and into said base, and at least one other mechanical adjustment member extending through said second top plate flange and said second bottom plate flange and into said base, whereby manipulation of said mechanical adjustment members adjusts the distance between said first top plate flange and said first bottom plate flange and between said second top plate flange and said second bottom plate flange, thereby adjusting the distance between said mold cavity top wall and said mold cavity bottom wall.

The invention may be further defined as such a device wherein said mechanical adjustment members may be independently manipulated, such that the distance between said first top plate flange and said first bottom plate flange may be different from the distance between said second top plate flange and said second bottom plate flange, and further comprising at least one compressible resilient member disposed between said first top plate flange and said first bottom plate flange, and at least one resilient member disposed between said second top plate flange and said second bottom plate flange, and further wherein said mold cavity bottom wall is generally convex and said mold cavity top wall is generally concave, and further wherein said top plate nests within said bottom plate, and further wherein said recess is four-sided, and further comprising a plurality of said top mold plates and a plurality of said bottom mold plates, wherein said mold cavity top wall of each said top mold plate is different in curvature, configuration or shape and wherein said mold cavity bottom wall of each said bottom mold plate is different in curvature, configuration or shape.

The methodology comprises the steps of removing a portion of cranial bone that requires replacement to create a defined cranial opening in the cranium. The measurements of the removed cranial bone or of the remaining cranial edges are then taken to determine the necessary size, configuration, curvature and thickness of the implant to approximate the defined opening. The proper bottom and top mold plates 12 and 13 are chosen to best match the dimensions of the cranial opening, and the top mold plate 13 is adjusted relative to the bottom mold plate 12 to best match the edge thickness or thicknesses of the removed portion. The implant is then prepared and cured, removed from the mold, and further shaped or processed as required to optimize the replacement match. The implant is then positioned in the cranial opening and secured to the cranium using known methodologies, such as with adhesives, other bonding materials or mechanical fasteners.

With reference now to the drawings, the cranial implant molding device 10 comprises a base or frame member 11 having a central recess 19, preferably four-sided, to receive a paired set of mold plates 12 and 13. The base 11 receives and retains a bottom mold plate 12 and a top mold plate 13 in separated manner such that in combination the two plates 12 and 13 define a generally centralized mold cavity 20 to receive an implant forming material. The bottom mold plate 12 comprises a mold cavity bottom wall 23, the mold cavity bottom wall 23 being generally convex on the side facing the mold cavity 20 and top mold plate 13. The bottom mold plate 12 further comprises first and second flanges 14 positioned on opposing sides of the mold cavity bottom wall 23, the bottom plate flanges 14 joined to the mold cavity bottom wall 23 by depending walls 25. In a basic embodiment the bottom mold plate 12 may be permanently affixed to the base 11. The top mold plate 13 comprises a mold cavity top wall 22, the mold cavity top wall 22 being generally concave on the side facing the mold cavity 20 and bottom mold plate 12, with the mold cavity top wall 22 provided with a venting port 18. The top mold plate 13 further comprises first and second flanges 15 positioned on opposing sides of the mold cavity top wall 23, the top plate flanges 15 joined to the mold cavity top wall 22 by depending walls 24. The mold cavity top wall 22 and mold cavity bottom wall 23 are positioned below the height of the flanges 14 and 15, and the top wall flange 15 will extend inwardly slightly farther than the bottom wall flange 14, such that the top plate depending walls 24 are received within the bottom plate depending walls 25 and the top mold plate 13 is generally nested within the bottom mold plate 12.

The molding device 10 is preferably capable of receiving a number of mold plates 12 and 13 possessing having mold cavity top walls 22 and mold cavity bottom walls 23 of different shapes, curvatures, sizes, etc., such that implants of varying shapes and sizes may be produced. The mold cavity walls 22 and 23 may also be provided with projections or depressions to create additional surface features in the implant. Thus, the molding device 10 may be a component of a kit that possesses multiple sets of mold plates 12 and 13.

At least one mechanical adjustment member 17, and possibly multiple mechanical adjustment members 17, is provided on each side of base 11. As shown in the drawings, the mechanical adjustment members may comprise threaded bolts received within threaded bores 21, where the threaded portions extend through apertures disposed in the first flanges 14 and 15 and the second flanges 14 and 15. The top plate flanges 15 may be secured to upper portion of the mechanical adjustment members 17 such that rotation of the mechanical adjustment members 17 raises or lowers the top plate 13 relative to the bottom plate 12. Alternatively, the top plate flanges 15 may not be directly connected to the mechanical adjustment members 16, in which case the implant forming material disposed in the mold cavity 20 serves to provide upward pressure against the top plate 13.

Most preferably, one or more compressible, resilient members 16, such as for example circular washers, rectangular pads, springs or similar members, are positioned between the first flanges 14 and 15 and between the second flanges 14 and 15. With this structure the compressible resilient members 16 provide upward pressure against the top plate flanges 15 such that the top plate flanges 15 do not require connection to the mechanical adjustment members 17. Manipulation of the mechanical adjustment members 17 to vary the separation distance of the top plate 13 from the bottom plate 12 results in compression or expansion of the compressible resilient members.

To create an implant, the appropriate bottom and top mold plates 12 and 13 that most closely approximate the desired curvature, shape and lateral dimensions of the removed cranial bone segment are selected and the bottom mold plate 12 is positioned on the base 11. Implant forming material, such as a liquid, putty or cement of any type suitable for the formation of biocompatible implants, is then placed, poured, injected, sprayed or otherwise deposited onto the bottom mold plate 12. The compressible resilient members 16, if utilized, are then properly positioned on the bottom plate flanges 14 and the top mold plate 13 is placed onto the base 11. The mechanical adjustment members 17 are inserted through the flanges 14 and 15 and the compressible resilient members 16 and into the bores 21 in base 11. The mechanical adjustment members 17 are then manipulated to press the top plate 13 toward the bottom plate 12 to compress and distribute the implant forming material within the mold cavity 20, excess implant forming material being able to escape through the venting port 18 and be retained within the base recess 19. The top plate 13 is lowered to the desired separation distance relative to the bottom plate 12, equal on both sides to produce an implant having equal edge dimensions and varying to produce an implant having opposing edges of different thicknesses. Once the implant forming material has sufficiently cured, the top plate 13 is removed and the implant is released from the bottom plate 12.

In an alternative method for creating a cranial implant, the appropriate bottom and top mold plates 12 and 13 that most closely approximate the desired curvature, shape and lateral dimensions of the removed cranial bone segment are selected and positioned on the base 11, and the mechanical adjustment members 17 are inserted through flanges 15, the compressible resilient members 16 and flanges 14 and into the bores 21. Where the edge thicknesses of the cranial implant are to be equal on both sides, the separation distance between the first flanges 14 and 15 and between the second flanges 14 and 15 are set to the desired equal distance. Where one side of the implant is to be thinner than the other, the separation distance of the set of first flanges 14 and 15 on one side of the mold cavity 20 is set to one dimension and the set of second flanges 14 and 15 on the other side of the mold cavity 20 is set to a different dimension. Implant forming material is then injected, extruded, poured or otherwise introduced through vent port 18 into the mold cavity 20 defined by the two mold plates 12 and 13. The venting port 18 also serves to release volatiles or any excess or expanding implant forming material, which is retained within the base recess 19. Any properly biocompatible implant forming material may be used, such as a putty or cement previously approved for medical purposes, that upon curing or hardening produces a substantially rigid, structurally strong implant. For example, and not meaning to be limiting in any way, a bone cement marketed under the brand name KRYPTONITE by Doctor's Research Group, Inc., has been shown to be suitable for this purpose. Once the implant has cured, the top mold plate 13 is removed and the implant is available for further processing if needed prior to implantation.

It is understood that equivalents and substitutions to certain elements and structures set forth above may be obvious to those of ordinary skill in the art, and the embodiments and examples as described are not meant to be limiting. Therefore the true scope and definition of the invention is to be as set forth in the following claims.

We claim:

1. A method of cranial repair comprising the steps of:
    removing a portion of cranial bone to create a defined opening in the cranium;
    measuring the removed portion or the remaining cranial edges to determine the dimensions, shape and edge thicknesses of the removed portion;
    providing a cranial implant molding device comprising a bottom plate comprising a generally convex mold cavity bottom wall, a first and a second bottom plate flange positioned to either side of said mold cavity bottom wall, and a depending wall connecting each of said bottom plate flanges to said mold cavity bottom wall; a top plate comprising a generally concave mold cavity top wall, a first and a second top plate flange positioned to either side of said mold cavity top wall, a depending wall connecting each of said top plate flanges to said mold cavity top wall, and a vent port disposed in said mold cavity top wall; a base comprising a recess, said bottom plate and said top plate being positioned on said base such that said mold cavity bottom wall and said mold cavity top wall are disposed within said recess and such that said mold cavity bottom wall is separated from said mold cavity top wall to form a mold cavity adapted to receive implant forming material; at least one compressible resilient member disposed between said first top plate flange and said first bottom plate flange, and at least one resilient member disposed between said second top plate flange and said second bottom plate flange; at least one mechanical adjustment member extending through said first top plate flange and said first bottom plate flange and into said base, and at least one other mechanical adjustment member extending through said second top plate flange and said second bottom plate flange and into said base, whereby manipulation of said mechanical adjustment members adjusts the distance between said first top plate flange and said first bottom plate flange and between said second top plate flange and said second bottom plate flange, thereby adjusting the distance between said mold cavity top wall and said mold cavity bottom wall; wherein said mechanical adjustment members may be independently manipulated, such that the distance between said first top plate flange and said first bottom plate flange may be different from the distance between said second top plate flange and said second bottom plate flange;
    creating a cranial implant by delivering said implant forming material into said mold cavity;
    adjusting the separation distance between said bottom mold plate and said top mold plate;
    allowing said implant to cure and removing said implant from said cranial implant molding device; and
    positioning said implant in said cranial defined opening and securing said implant.

2. The method of claim 1, further comprising the steps of providing a plurality of said top mold plates and a plurality of said bottom mold plates, wherein said mold cavity top wall of each said top mold plate is different and wherein said mold cavity bottom wall of each said bottom mold plate is different; and
    choosing one of said bottom mold plates and one of said top mold plates that best matches said defined opening.

3. The method of claim 1, wherein said step of adjusting the separation distance between said bottom mold plate and said top mold plate is performed prior to said step of creating a cranial implant by delivering said implant forming material into said mold cavity.

4. The method of claim 1, wherein said step of adjusting the separation distance between said bottom mold plate and said top mold plate is performed after said step of creating a cranial implant by delivering said implant forming material into said mold cavity.

5. The method of claim 1, wherein said step of adjusting the separation distance between said bottom mold plate and said top mold plate comprises manipulating said mechanical adjustment member such that the separation distance between said first top plate flange and said first bottom plate flange is different from the distance between said second top plate flange and said second bottom plate flange.

6. The method of claim 1, wherein said step of adjusting the separation distance between said bottom mold plate and said top mold plate comprises manipulating said mechanical adjustment member such that the separation distance between said first top plate flange and said first bottom plate flange is the same as the distance between said second top plate flange and said second bottom plate flange.

* * * * *